(12) United States Patent
Yoshida

(10) Patent No.: US 10,918,784 B2
(45) Date of Patent: Feb. 16, 2021

(54) HOLDING MEMBER AND PACKAGING STRUCTURE OF CHEMICAL CONTAINER PARTS

(71) Applicant: DAIKYO SEIKO, LTD., Tochigi (JP)

(72) Inventor: Takayuki Yoshida, Tochigi (JP)

(73) Assignee: DAIKYO SEIKO, LTD., Tochigi (JP)

( * ) Notice: Subject to any disclaimer, the term of this patent is extended or adjusted under 35 U.S.C. 154(b) by 58 days.

(21) Appl. No.: 16/230,043

(22) Filed: Dec. 21, 2018

(65) Prior Publication Data

US 2019/0240395 A1 Aug. 8, 2019

(30) Foreign Application Priority Data

Feb. 8, 2018 (JP) .............................. JP2018-020755

(51) Int. Cl.
*B65D 83/10* (2006.01)
*A61M 5/00* (2006.01)
(Continued)

(52) U.S. Cl.
CPC ................ *A61M 5/002* (2013.01); *A61J 1/16* (2013.01); *A61M 5/008* (2013.01); *A61M 5/31511* (2013.01)

(58) Field of Classification Search
CPC ....... B65D 85/62; A61M 5/002; A61M 5/008; A61M 5/31511; A61J 1/16
(Continued)

(56) References Cited

U.S. PATENT DOCUMENTS 4,349,109 A * 9/1982 Scordato ................. B01L 9/543
206/486
8,800,800 B2 * 8/2014 Gerner .................. A61M 5/008
211/71.01
(Continued)

FOREIGN PATENT DOCUMENTS

EP 1990068 11/2008
EP 2119463 11/2009
(Continued)

OTHER PUBLICATIONS

Japanese Office Action, issued in the corresponding Japanese patent application No. 2018-020755, dated Apr. 16, 2019, 3 pages.
(Continued)

*Primary Examiner* — Luan K Bui
(74) *Attorney, Agent, or Firm* — Hamre, Schumann, Mueller & Larson, P.C.

(57) ABSTRACT

A holding member with a sheet-shaped substrate portion having first and second surface; and plural storage portions in a cylinder shape, each penetrating the first and second surfaces of the substrate portion, and each protruding on a first surface side, is provided. The storage portions each comprise a first opening end portion for loading and unloading a container part at a protruded tip of each storage portion; a bulging portion where an inner wall face on a first opening end portion side bulges continuously from the first opening end portion toward inside the cylinder-shaped portion, thereby forming an opening widened toward the first opening end portion; a second opening end portion at a base end formed by the second surface of the substrate portion; and a tapered-off portion where the inner wall face narrows on a second opening end portion side, an opening thereof toward its end.

14 Claims, 8 Drawing Sheets

(51) Int. Cl.
*A61J 1/16* (2006.01)
*A61M 5/315* (2006.01)

(58) Field of Classification Search
USPC .................................. 206/363, 366, 438, 499
See application file for complete search history.

(56) References Cited

U.S. PATENT DOCUMENTS

| | | | |
|---|---|---|---|
| 2009/0095647 A1* | 4/2009 | Togashi | A61M 5/008 206/438 |
| 2011/0192756 A1* | 8/2011 | Hill | A61M 5/008 206/515 |
| 2017/0348476 A1* | 12/2017 | Thompson | A61M 5/001 |
| 2018/0235838 A1 | 8/2018 | Kawamura | |
| 2019/0030236 A1* | 1/2019 | Okihara | B65B 55/06 |

FOREIGN PATENT DOCUMENTS

| | | |
|---|---|---|
| WO | 2009/015862 | 2/2009 |
| WO | 2007/099649 | 7/2009 |
| WO | 2008/107961 | 6/2010 |
| WO | 2010/062602 | 6/2010 |
| WO | 2013/084791 | 6/2013 |
| WO | 2014/009037 | 1/2014 |
| WO | 2016/111698 | 7/2016 |
| WO | 2017/038878 | 3/2017 |
| WO | 2017/188427 | 11/2017 |

OTHER PUBLICATIONS

Extended European Search Report, issued in the corresponding European patent application No. 19154783.5, dated May 15, 2019, 7 pages.

Second Japanese Office Action, issued in the corresponding Japanese patent application No. 2018-020755, dated Jul. 9, 2019, 4 pages.

Third Japanese Office Action, issued in the corresponding Japanese patent application No. 2018-020755, dated Oct. 8, 2019, 8 pages (including machine translation), the cited references being previously provided in IDS.

European Office Action, issued in the corresponding European patent application No. 19154783.5, dated Aug. 21, 2020, 6 pages.

\* cited by examiner

[FIG. 1A]
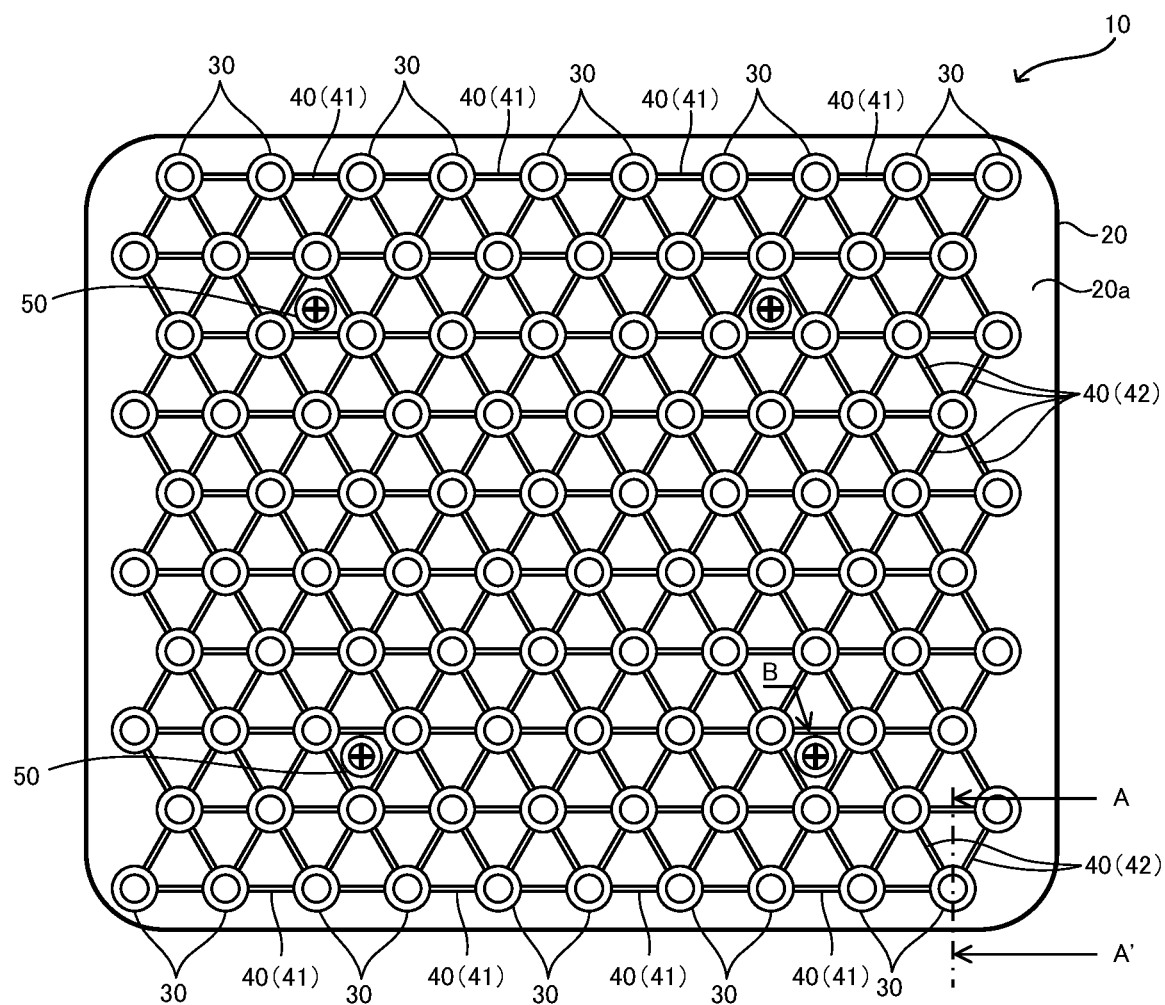

[FIG. 1B]
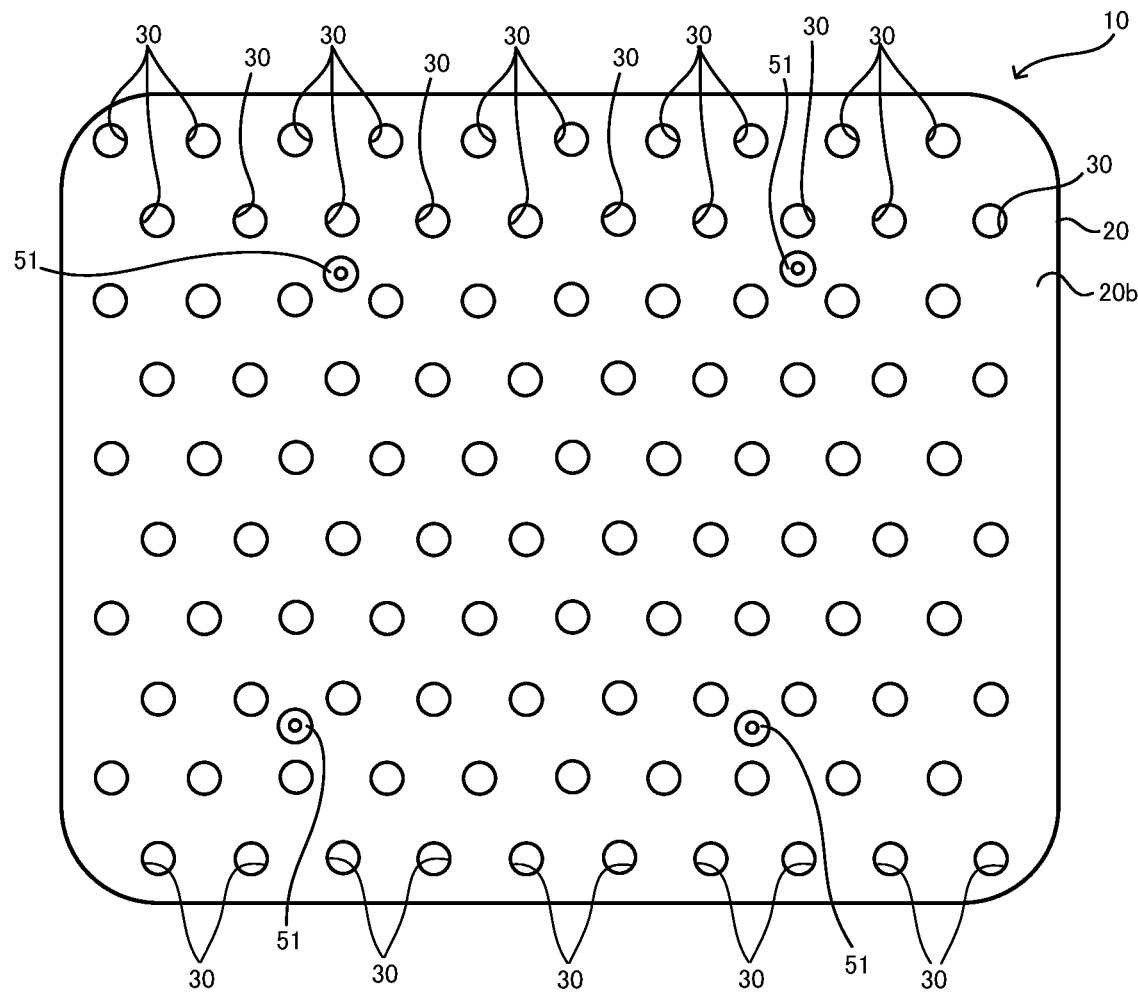
[FIG. 1C]
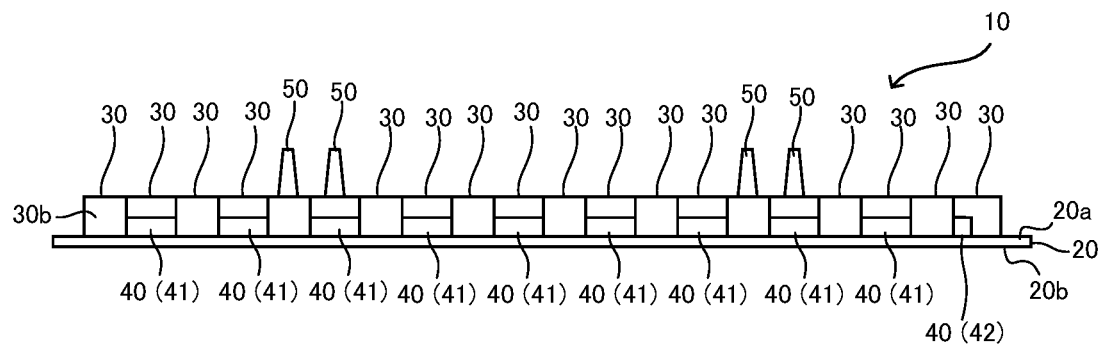

[FIG. 1D]
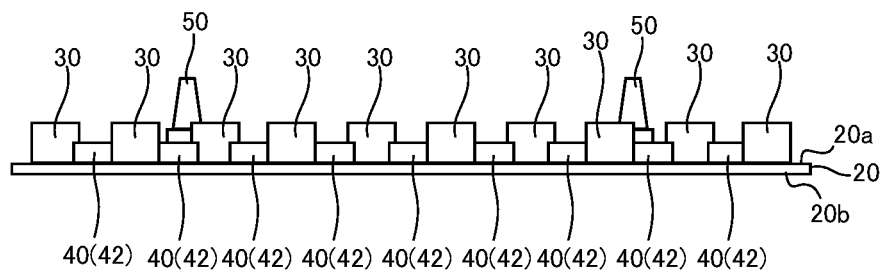
[FIG. 1E]
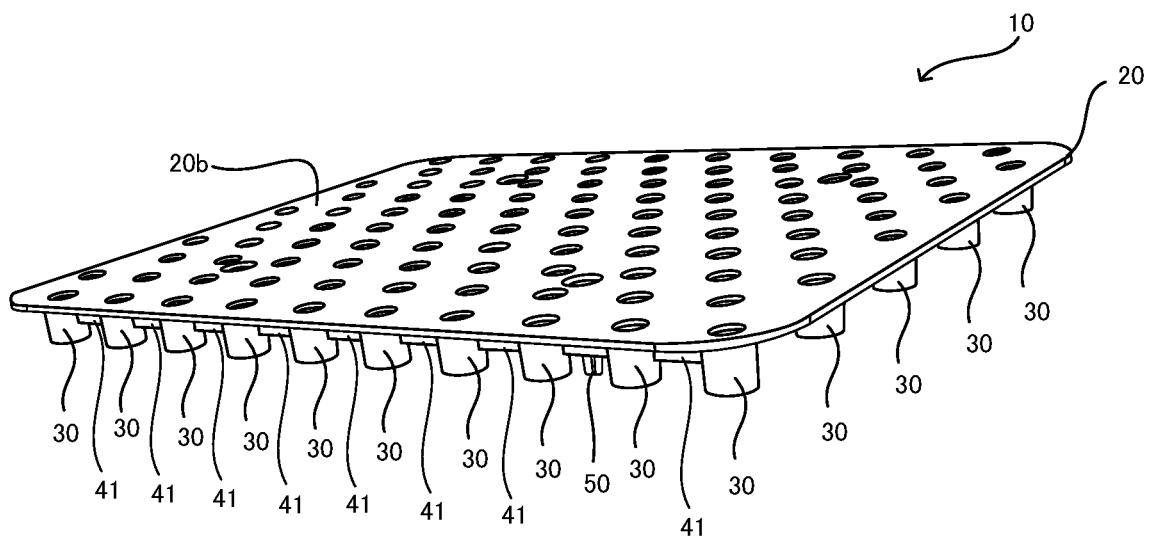

[FIG. 2]
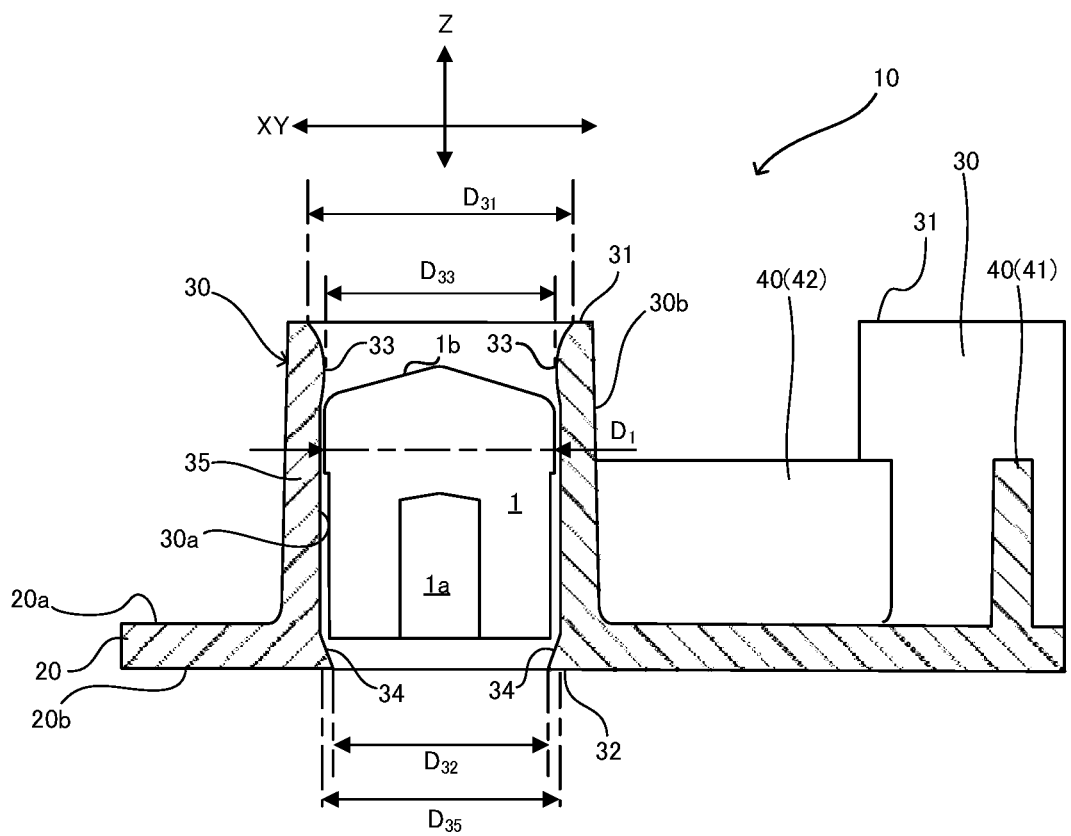

[FIG. 3]
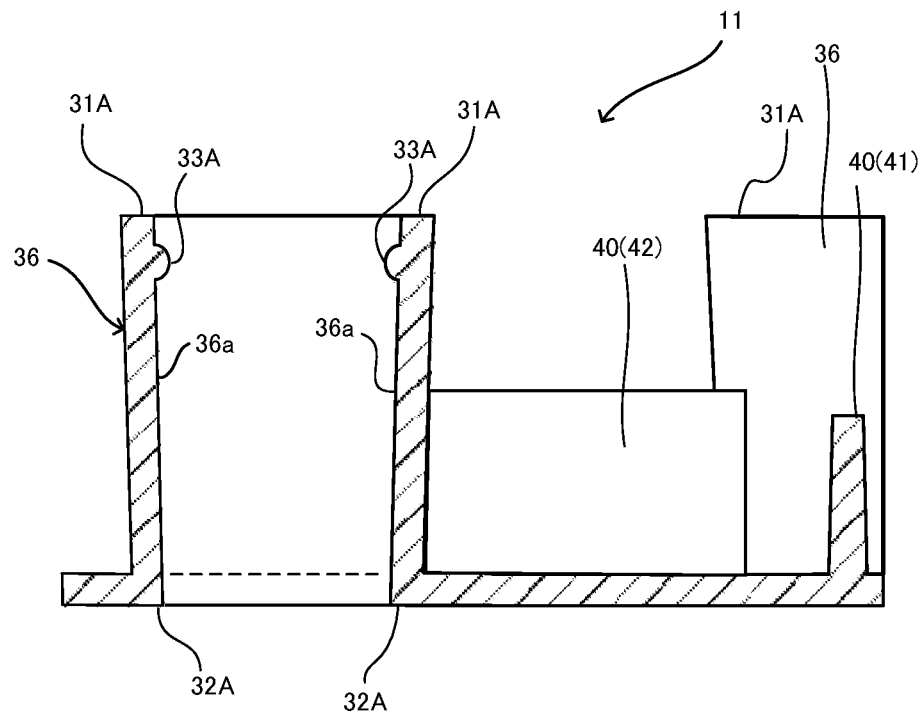
[FIG. 4]
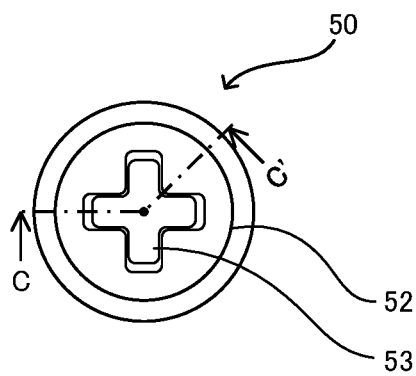

[FIG. 5]
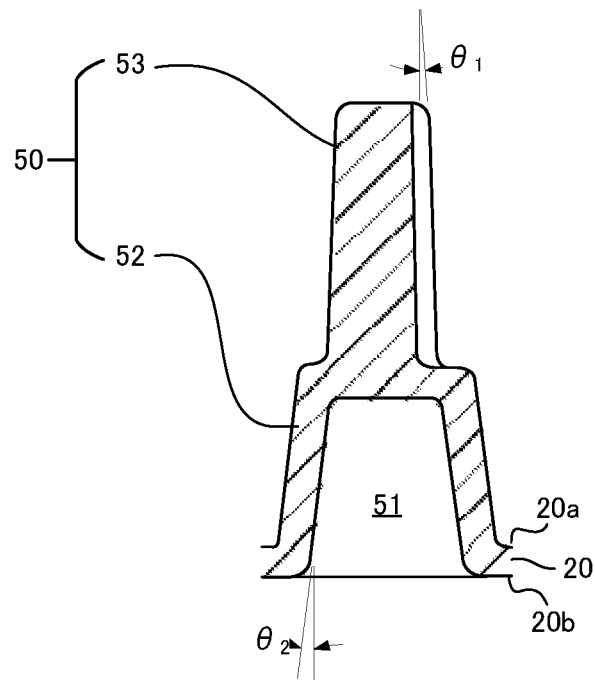
[FIG. 6]
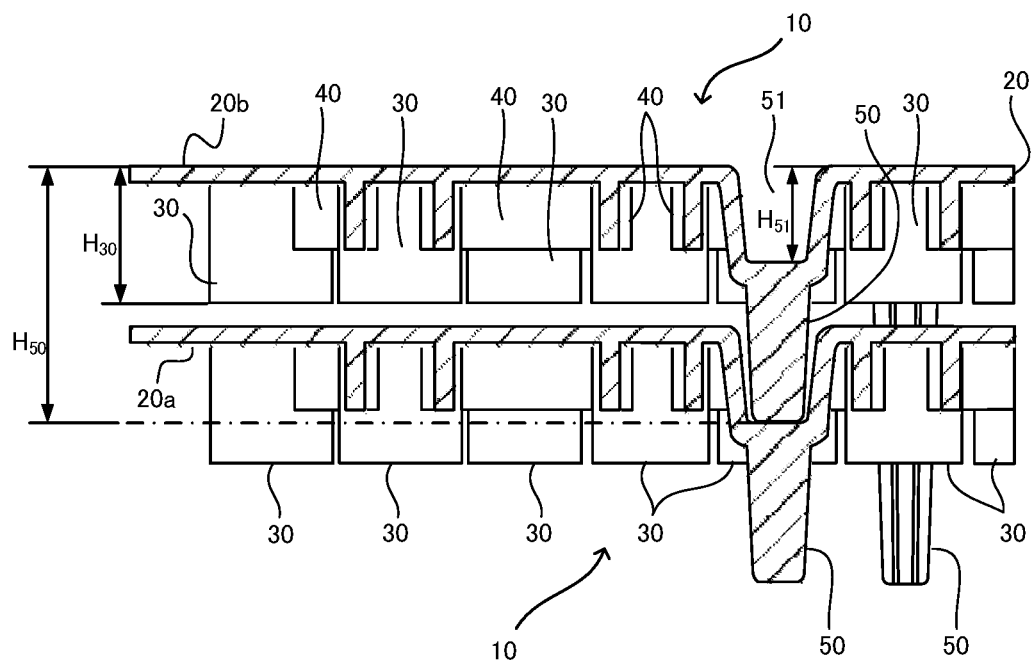

[FIG. 7]
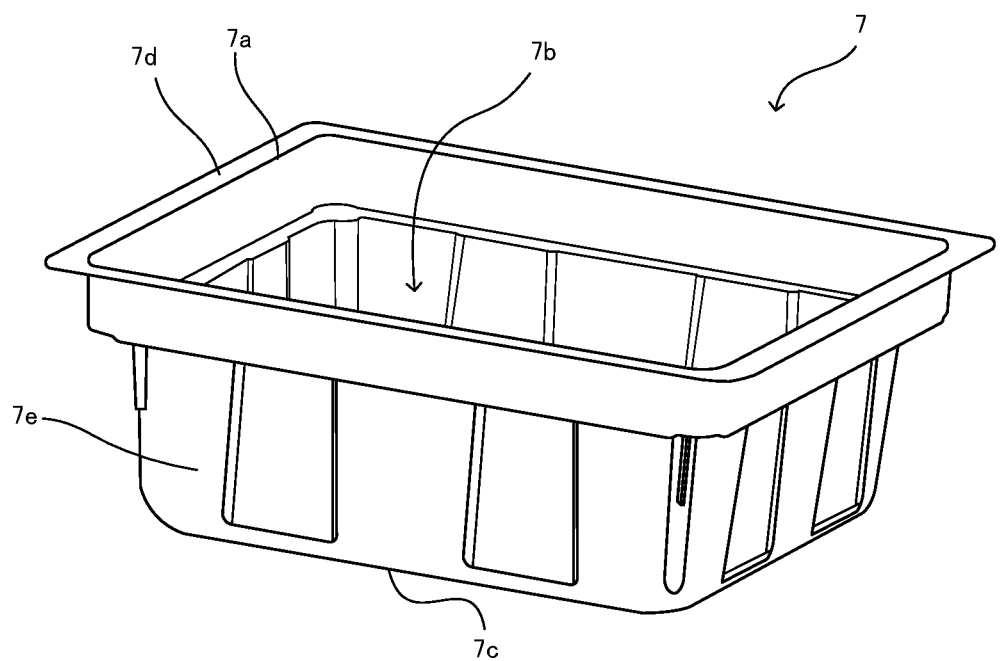

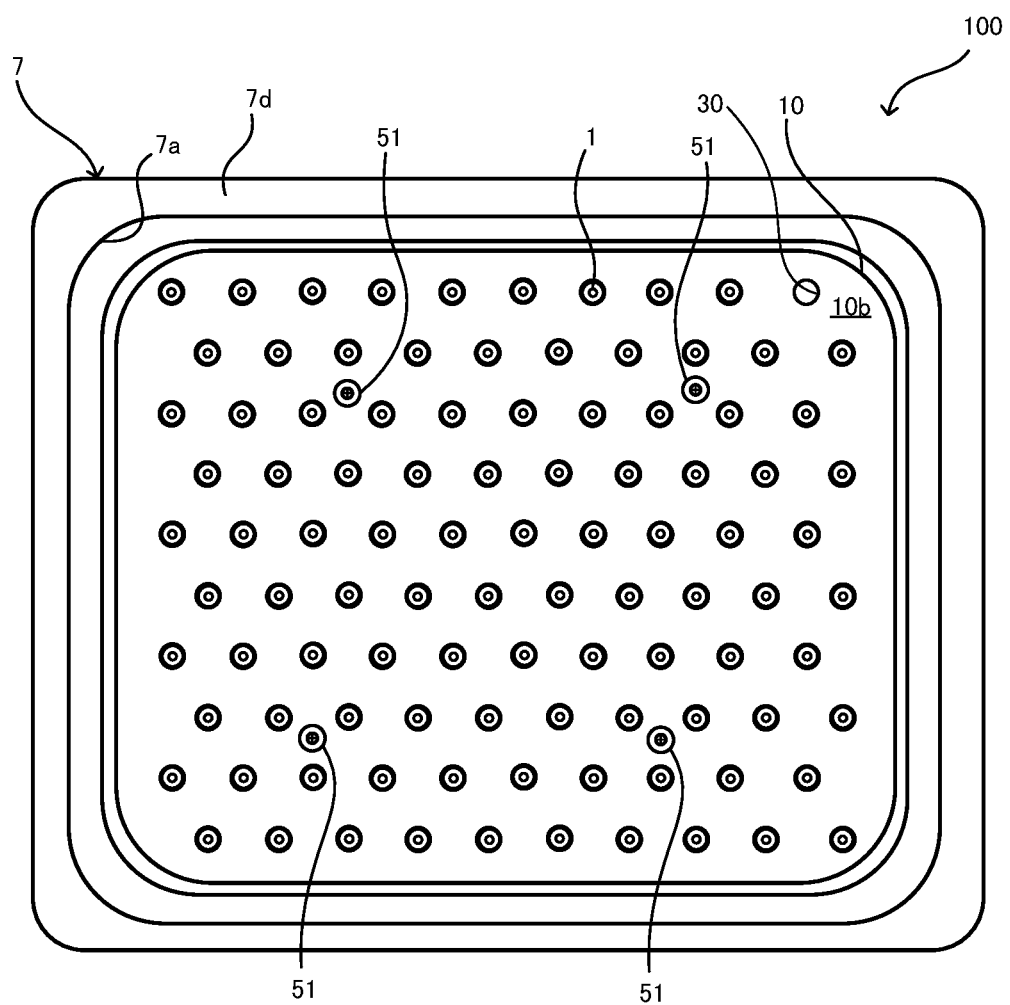
[FIG. 8]

HOLDING MEMBER AND PACKAGING STRUCTURE OF CHEMICAL CONTAINER PARTS

BACKGROUND OF THE INVENTION

Field of the Invention

The present invention relates to a holding member and a packaging structure of chemical container parts.

Description of the Related Art

Parts constituting chemical containers such as a syringe and a vial are generally subjected to a sterilization treatment in the same manner as in the chemical containers by high-pressure steam sterilization or the like before being assembled into the chemical containers. In performing a sterilization treatment, storage, and conveyance of a chemical container part, or in assembling a chemical container part into a chemical container or performing other processes, a holding member, also called a nest, which can simultaneously hold a plurality of chemical container parts is used. In addition, in performing a sterilization treatment, storage, conveyance of a chemical container part, or performing other processes, a box type container in which a holding member holding a plurality of chemical container parts is accommodated is used.

For example, International Publication No. WO 2007099649 discloses a syringe piston nest characterized by including: a substrate; and a plurality of cylindrical syringe piston storage portions each penetrating the substrate vertically to the substrate with a side of one face of the substrate being as one opening end and each being protruded from an opposition side of the substrate. It is described in International Publication No. WO 2007099649 that by this syringe piston nest, steam sterilization can be performed in a state in which a syringe piston is stored in a piston storage portion.

In addition, International Publication No. WO 2008107961 for example discloses a medical container having at least: a container main body; and a holding member to be installed inside the container main body, in which the holding member is at least provided with a plurality of cylindrical holding portions for holding injection cylinders. It is described in International Publication No. WO 2008107961 that by using this medical container, a gas for sterilization can be filled in the container and a sterilization treatment of injection cylinders each being held by a holding portion in the holding member installed in the container can be performed.

SUMMARY OF THE INVENTION

In International Publication No. WO 2007099649 described above, there is proposed a syringe piston nest in which a depression formed along a circumferential direction at a same circumferential face of a portion of an outer circumferential face of a piston and a bulging portion formed at a portion of an inner circumferential face of the piston storage portion by allowing an inner wall face of a piston storage portion to bulge toward an inside are engaged. According to this constitution, a piston stored in the piston storage portion can be fixed to the piston nest.

However, in a case where a piston or another part in which there is no depression or in which a depression is very small is an object of holding, the above-described engagement method cannot be adopted. Therefore, it becomes beneficial if a holding member can be provided which can hold a chemical container part without adopting an engagement method so that a part not having a depression or a part having a very small depression can also be dealt with.

In addition, it is required for a holding member for holding a plurality of chemical container parts that the parts are each easily inserted in a cylindrical storage portion (holding portion), that sudden detachment of a part stored in the storage portion is unlikely to occur, and that a sterilization treatment can be effectively performed to parts stored in the storage portion.

Thus, the present invention intends to provide a holding member in which a chemical container part is easily loaded into and unloaded from a storage portion, which can suppress sudden detachment of the part from the storage portion, and in which a sterilization treatment of a part can be effectively performed.

The present invention provides a holding member provided with: a sheet-like substrate portion having a first surface and a second surface; and a plurality of storage portions each penetrating the first surface and the second surface of the substrate portion and each protruding in a direction of a side of the first surface and in a form of a cylinder where a chemical container part is to be stored, wherein the storage portions are each provided with: a first opening end portion forming a loading and unloading mouth for the part at a protruded tip of each of the storage portions; a bulging portion where an inner wall face of each of the storage portions on a side of the first opening end portion bulges continuously from the first opening end portion in a direction of an inside of the cylinder, thereby forming an opening widened toward the first opening end portion; a second opening end portion formed at a base end of each of the storage portions by the second surface of the substrate portion; and a tapered-off portion where the inner wall face of each of the storage portions on a side of the second opening end portion is formed in such a way as to narrow toward the second opening end portion.

In addition, the present invention provides a holding member provided with: a sheet-like substrate portion having a first surface and a second surface; and a plurality of storage portions each penetrating the first surface and the second surface of the substrate portion and each protruding in a direction of a side of the first surface and in a form of a cylinder where a chemical container part is to be stored, wherein the storage portions are each provided with: a first opening end portion forming a loading and unloading mouth for the part at a protruded tip of each of the storage portions; a bulging portion where an inner wall face of each of the storage portions on a side of the first opening end portion bulges in a direction of an inside of the cylinder; and a second opening end portion formed at a base end of each of the storage portions by the second surface of the substrate portion, and in a size in a direction orthogonal to an axial direction of the cylinder of each of the storage portions, an inner size of the first opening end portion and an inner size of an intermediate portion between the bulging portion and the second opening end portion are larger than an outer size of the part, and an inner size at a position where the bulging portion is provided and an inner size of the second opening end portion are smaller than the outer size of the part.

According to the present invention, a holding member in which a chemical container part is easily loaded into and unloaded from a storage portion, which can suppress sudden detachment of the part from the storage portion, and in which a sterilization treatment of a part can be effectively performed can be provided.

BRIEF DESCRIPTION OF THE DRAWINGS

FIG. 1A is a diagram illustrating a holding member according to one embodiment of the present invention and is a plan view of the holding member viewed from a side of a first surface of a substrate portion;

FIG. 1B is a plan view (bottom view) of the holding member viewed from a side of a second surface of the substrate portion in the holding member illustrated in FIG. 1A;

FIG. 1C is a front view of the holding member illustrated in FIG. 1A;

FIG. 1D is a side view of the holding member illustrated in FIG. 1A;

FIG. 1E is a perspective view of the holding member illustrated in FIG. 1A;

FIG. 2 is a sectional view taken along the A-A' line illustrated in FIG. 1A and is a diagram illustrating a state in which a chemical container part is stored in a storage portion in the holding member;

FIG. 3 is a sectional view corresponding to FIG. 2, the sectional view illustrated for describing one example of constitution according to a modification example of a storage portion in a holding member;

FIG. 4 is a diagram for describing constitution of a supporting pillar in a holding member according to one embodiment of the present invention and is an enlarged view of the region B illustrated in FIG. 1A;

FIG. 5 is a sectional view taken along the C-C' line illustrated in FIG. 4;

FIG. 6 is an enlarged sectional view illustrating a state in the vicinity of supporting pillars and recessed portions at the time when two holding members each provided with supporting pillars and recessed portions in one embodiment of the present invention are stacked;

FIG. 7 is a perspective view illustrating one example of a box type container which can be used for a packaging structure of chemical container parts according to one embodiment of the present invention; and FIG. 8 is a plan view of a packaging structure using the box type container illustrated in FIG. 7, the plan view viewed from a side of an opening portion of the box type container.

DETAILED DESCRIPTION OF THE PREFERRED EMBODIMENTS

Hereinafter, embodiments of the present invention will be described with reference to the accompanying drawings, but the present invention is not limited to the following embodiments. It is to be noted that the common constitution in respective figures is denoted as the same reference sign, and overlapped description may be omitted in some cases.

<Holding Member>

FIGS. 1A to E (hereinafter, these may be sometimes collectively referred to as FIG. 1) are diagrams each illustrating a holding member 10 according to one embodiment of the present invention. FIG. 1A is a plan view of the holding member 10 viewed from the side of a first surface 20a of a substrate portion 20. FIG. 1B is a plan view (bottom view) of the holding member 10 viewed from the side of a second surface 20b of the substrate portion 20. FIG. 1C is a front view (rear view is the same) of the holding member 10. FIG. 1D is a right side view (left side view is the same) of the holding member 10. FIG. 1E is a perspective view of the holding member 10.

As illustrated in FIG. 1, the holding member 10 is provided with a sheet-like substrate portion 20 having a first surface 20a and a second surface 20b. In addition, the holding member 10 is provided with a plurality of storage portions 30 each penetrating the first surface 20a and the second surface 20b of the substrate portion 20 and each protruding in a direction of a side of the first surface 20a and in a form of a cylinder where a chemical container part is to be stored.

A chemical container part (in the present specification, sometimes simply referred to as "part") is stored in a cylinder (inside of cylinder) of the storage portion 30, and the holding member 10 can thereby hold a plurality of parts according to the number of the storage portions 30. Such a holding member 10 is also called a nest. A part can be stored in each of the storage portions 30 in the holding member 10 such that the part can be loaded and unloaded.

In a state in which a plurality of parts are held by the holding member 10, storage, conveyance, a sterilization treatment of the parts, assembly of a chemical container, and other processes can be performed. Therefore, damage, contamination, and the like to the parts can be suppressed on these occasions. For example, a sterilization treatment, assembly with another part for assembling a chemical container, and other processes can be performed in a state in which a part is stored in each storage portion 30 in the holding member 10. Examples of the sterilization treatment include radiation sterilization by an electron beam, a γ-ray, or the like, high-pressure steam sterilization using an autoclave, and gas sterilization using an ethylene oxide gas or the like. In addition, examples of the assembly with another part include a method in which all the parts stored in the respective storage portions 30 in the holding member 10 are perforated all at once with an automatic assembler in an isolator to be each assembled to another part.

As a chemical container part, a chemical container part, a part to be subjected to a sterilization treatment, a part made of elastomer, and the like the whole size of which can be accommodated in the storage portion 30 in the holding member 10 are suitable. Examples of such parts include parts for an injector and a vial as chemical containers. Specific, suitable examples of the parts include a cap, a stopper, a lid, and a syringe piston, and among these a syringe piston is more suitable.

The substrate portion 20 and the storage portion 30 may be formed by different materials; however, it is preferable that the substrate portion 20 and the storage portion 30 be integrally formed by the same material such as the same resin or the same metal. When the holding member 10 is produced by molding a resin material, or a thermoplastic resin among others, the substrate portion 20 and the storage portion 30 can be integrally formed simply and at a low cost.

The resin material for forming the holding member 10 (substrate portion 20 and storage portion 30) is not particularly limited, and examples of suitable resin materials include polyolefin-based resins such as polyethylene and polypropylene. Also, the method for molding the holding member 10 is not particularly limited, for example, known molding methods such as injection molding, vacuum forming, and pressure forming can be adopted, and injection molding is more suitable. It is to be noted that the storage portion 30 both ends of which are open is separately prepared in advance, and the storage portion 30 which is separately prepared may be installed at each through hole of the substrate portion 20 in which a plurality of through holes are drilled at predetermined intervals.

The shape in planar view, the size, and the thickness of the sheet-like substrate portion 20 are not particularly limited. The shapes in planar view of the first surface 20a and the second surface 20b of the substrate portion 20 may be an approximately circular shape, an approximately elliptical shape, an approximately polygonal shape, and the like in addition to an approximately rectangular shape as illustrated in the figures. The holding member 10 is preferably accommodated in a box type container, which will be described later, to be conveyed or subjected to other processes, and therefore the shapes in planar view of the substrate portion 20 and the holding member 10 preferably correspond to the shape in planar view of the box type container and are more preferably approximately rectangular shapes corresponding to the shape in planar view of the box type container. In a case where the shape in planar view of the substrate portion 20 is an approximately rectangular shape, examples of the size of the substrate portion 20 include a size of each side being about 100 to about 500 mm. In addition, from the viewpoint of constituting the holding member 10 having light weight and strength to endure the use, the thickness of the substrate portion 20 is preferably about 0.5 to about 5 mm.

The storage portion 30 preferably has a cylindrical shape corresponding to the shape of a chemical container part to be stored in the storage portion 30. For example, in a case where the part has an approximately columnar shape or an approximately cylindrical shape, the storage portion 30 can be formed in the form of a cylinder, and in a case where the part has an approximately square pillar shape or an approximately square cylindrical shape, the storage portion 30 can be formed into a square cylindrical shape. In FIG. 1, the holding member 10 provided with cylindrically shaped storage portions 30 is illustrated as an example.

In the holding member 10, a plurality of storage portions 30 are preferably provided at approximately equal intervals in such a way as to have a predetermined interval between adjacent storage portions 30, and are more preferably arranged in a staggered form (see FIGS. 1A and B) or arranged in a lattice form (not illustrated in figures) to the substrate portion 20. A plurality of parts can be regularly disposed on a plane of the same level by such a holding member 10. A plurality of storage portions 30 are still more preferably arranged in a staggered form to the substrate portion 20 because a large number of storage portions 30 are easily provided.

The number of the storage portions 30 in the holding member 10 corresponds to the number of parts which one holding member 10 can hold, and the number of these storage portions 30 is not particularly limited. From the viewpoint that it is more efficient when a larger number of parts can be subjected to a sterilization treatment, conveyed, etc. at once, 20 (for example, arrangement of 4×5) or more storage portions 30 can be preferably provided for example. For example, 30 (for example, arrangement of 5×6), 42 (for example, arrangement of 6×7), 64 (for example, arrangement of 8×8), 100 (for example, arrangement of 10×10), 160 (for example, arrangement of 10×16) storage portions, or other numbers of storage portions 30 can be provided. In FIGS. 1A and B, an embodiment in which 100 storage portions 30 are arranged in a staggered form of 10×10 in longitudinal and transverse directions relative to the substrate portion 20 is illustrated as an example.

FIG. 2 is a sectional view taken along the A-A' line illustrated in FIG. 1A and illustrates a state in which a chemical container part 1 is stored in the storage portion 30 in the holding member 10. As the part 1, a suitable syringe piston (hereinafter, sometimes simply written as "piston") 1 is illustrated in the figure.

As illustrated in FIG. 2, the storage portion 30 is provided with: a first opening end portion 31 forming a loading and unloading mouth for the part 1 at a protruded tip of the storage portion 30; a second opening end portion 32 formed at a base end of the storage portion 30 by the second surface 20b of the substrate portion 20; and a bulging portion 33 where an inner wall face 30a of the storage portion 30 on a side of the first opening end portion 31 bulges in a direction of an inside of the cylinder.

The loading and unloading mouth formed by the first opening end portion 31 is an inserting mouth for the part 1 into the storage portion 30 and an unloading mouth for the part 1 inserted into the storage portion 30. Since the storage portion 30 is provided with the first opening end portion 31 and the second opening end portion 32 both of which are open to form a communicating cylindrical shape, steam, a gas, radial rays, and the like which can be used for a sterilization treatment easily get into the storage portion 30 so that a sterilization treatment can be performed to the part 1 stored in the storage portion 30. In addition, the part 1 stored in the storage portion 30 can be perforated in a direction from the opening of the second opening end portion 32 toward the loading and unloading mouth at the first opening end portion 31 using the above-described automatic assembler.

The bulging portion 33 may be the non-continuously formed bulging portion 33 in addition to the bulging portion 33 continuously formed in the form of a circle in a circumferential direction at the inner wall face 30a of the storage portion 30. Among these, the bulging portion 33 continuously formed in the form of a circle in the circumferential direction is preferable.

As described previously, the holding member 10 is more suitable as the piston holding member 10. Generally, a plunger is inserted in the piston 1, and the piston 1 is provided with a fixing hole (more suitably, screwing hole) for fixing the plunger inserted therein in some cases. In addition, a depression or a protruded portion for smoothly sliding the piston 1, which is fixed to the plunger, along a wall face inside of a barrel (injection cylinder) is provided in a circumferential direction at the outer circumferential face of the piston 1 in some cases. In inserting the piston 1 into the storage portion 30 in the holding member 10, the piston is preferably inserted into the loading and unloading mouth formed by the first opening end portion 31 of the storage portion 30 from the side of a fixing hole 1a of the piston 1. That is, when the piston 1 is stored in the storage portion 30, it is preferable that the fixing hole 1a of the piston 1 be positioned on the side of the second opening end portion 32 of the storage portion 30, and a liquid contact portion 1b (portion where piston 1 comes into contact with chemical liquid in syringe) of the piston 1 be positioned on the side of the first opening end portion 31 of the storage portion 30.

The conventional piston nest as described in Patent Literature 1 described previously adopts means for holding a piston in a storage portion by the engagement of a depression formed along the circumferential direction at the outer circumferential face of the piston to be stored in the storage portion and a bulging portion formed in the inner wall face of the storage portion. In contrast, the holding member 10 is provided with the storage portion 30, which will be described below, and thereby can hold the part 1 in the storage portion 30 even when the part 1 is a piston without a depression, a piston having a very small depression, or the like, and unintended detachment of the part 1 from the storage portion 30 can be suppressed. That is, the storage portion 30 in the holding member 10 has constitution of anyone or both of the first aspect and the second aspect, which will be described below, and the storage portion 30 preferably has constitution of both of the first aspect and the second aspect. In FIG. 2, the holding member 10 provided with the storage portion 30 having the constitution of both of the first aspect and the second aspect is illustrated as an example.

The storage portion 30 of the first aspect is a constitution aspect of the shape of the storage portion 30 itself. That is, as illustrated in FIG. 2, the storage portion 30 of the first aspect is provided with: a bulging portion 33 where the inner wall face 30a of the storage portion 30 on the side of the first opening end portion 31 bulges continuously from the first opening end portion 31 in the direction of the inside of the cylinder, thereby forming an opening widened toward the first opening end portion 31; and a tapered-off portion 34 where the inner wall face 30a of the storage portion 30 on the side of the second opening end portion 32 is formed in such a way as to narrow toward the second opening end portion 32.

In the storage portion 30 of the first aspect, the bulging portion 33 where the inner wall face 30a of the storage portion 30 on the side of the first opening end portion 31 bulges in the direction of the inside of the cylinder is continuously provided from the first opening end portion 31, thereby forming an opening widened toward the first opening end portion 31. Therefore, the loading and unloading mouth formed by the first opening end portion 31 widens, so that loading and unloading the part 1 into and from the storage portion 30 can be made easy. The bulging portion 33 exists on the side of the first opening end portion 31 which is a protruded tip of the storage portion 30, and therefore when the part 1 is loaded into and unloaded from the storage portion 30, the part 1 pushes the bulging portion 33 toward the outside of the cylinder and can slightly bend the storage portion 30.

In addition, the storage portion 30 of the first aspect is provided with the bulging portion 33 and the tapered-off portion 34, and therefore when the part 1 is stored in the storage portion 30 such that the whole part 1 falls therein, the bulging portion 33, the tapered-off portion 34, and the second opening end portion 32 function as a stopper for the part 1. Thereby, unintended detachment of the part 1 from the storage portion 30 can be suppressed. Further, this storage portion 30 is provided with the bulging portion 33 and the tapered-off portion 34 functioning as a stopper for the part 1, and therefore a portion between the bulging portion 33 and the tapered-off portion 34 in an axial direction Z of the cylinder of the storage portion 30 can be made to have a size by which a slight gap can be generated between the inner wall face 30a of the storage portion 30 and the part 1. Thereby, steam, a gas, and the like which can be used for a sterilization treatment diffuse around the part 1, and therefore the sterilization treatment can be performed to the part 1 sufficiently and effectively The storage portion 30 which satisfies the constitution of the second aspect, which will be described below, can also be obtained easily by inventing the constitution of the storage portion 30 of the first aspect.

The storage portion 30 of the second aspect is a constitution aspect of the storage portion 30 in terms of a viewpoint of the relationship with a chemical container part to be stored in the storage portion 30. That is, as illustrated in FIG. 2, in the size in the direction XY orthogonal to the axial direction Z of the cylinder of the storage portion 30, the inner size $D_{31}$ of the first opening end portion 31 and the inner size $D_{35}$ of an intermediate portion 35 between the bulging portion 33 and the second opening end portion 32 are constituted in such a way as to be larger than the outer size $D_1$ of the part 1. Besides, the storage portion 30 is such that the inner size $D_{33}$ at a position where the bulging portion 33 is provided (hereinafter, sometimes written as "inner size of the bulging portion") and the inner size $D_{32}$ of the second opening end portion 32 are constituted in such a way as to be smaller than the outer size $D_1$ of the part 1.

Any of the respective inner sizes $D_{31}$, $D_{32}$, $D_{33}$, and $D_{35}$, and the outer size $D_1$ of the part 1 is a size in the direction XY orthogonal to the axial direction Z of the cylinder of the storage portion 30. The inner size means a size of an inside, and the outer size means a size of an outside. The inner size $D_{31}$ of the first opening end portion 31 has the same meaning as the size of the loading and unloading mouth formed by the first opening end portion 31. The inner size $D_{32}$ of the second opening end portion 32 has the same meaning as the size of the opening formed by the second surface 20b of the substrate portion 20. The inner size $D_{33}$ at the position where the bulging portion 33 is provided means an inner size at a position where the bulging portion 33 bulges to the maximum in a direction of the inside of the cylinder. The intermediate portion 35 between the bulging portion 33 and the second opening end portion 32 means a regional portion, in the axial direction Z of the cylinder of the storage portion 30, from a portion corresponding to a base (or may also be referred to as foot or bottom) on the side of the second opening end portion 32 in the bulging portion 33 to a portion of the side of the second opening end portion 32 (including a case where the portion is the tapered-off portion 34), the portion being set in such a way as to have a size smaller than the outer size of the part 1. The median value in the range from the maximum value to the minimum value of the inner size of this regional portion is defined as the inner size $D_{35}$ of the intermediate portion 35.

Since the storage portion 30 in the holding member 10 illustrated in FIG. 1 and in FIG. 2 each have a cylindrical shape, each "inner size" in this case means an "inner diameter", but the storage portion 30 may have, for example, a square cylindrical shape or the like, and therefore the "inner size" is described in some cases in the present specification. In addition, since the part (syringe piston) 1 illustrated in FIG. 2 has an approximately columnar shape, the "outer size of the part" in this case means the "outer diameter of the part", but the part 1 may have, for example, a square pillar shape or the like, and therefore the "outer size of the part" is described in some cases in the present specification. Further, there are some cases where the outer size of the part 1 is not constant, such as a case where a depression is formed at the outer circumferential face, but in that case, the "outer size of the part" means the maximum outer size of the part 1 in the size in the direction XY orthogonal to the axial direction Z of the cylinder of the storage portion 30.

In the storage portion 30 of the second aspect, the inner size $D_{31}$ of the first opening end portion 31 forming the loading and unloading mouth for the part 1 at the protruded tip of the storage portion 30 is larger than the outer size $D_1$ of the part 1, and therefore the part 1 is easily loaded into and unloaded from the storage portion 30. The inner size $D_{33}$ of the bulging portion 33 is smaller than the outer size $D_1$ of the part 1, but the bulging portion 33 is provided on the side of the first opening end portion 31 which is a protruded tip of the storage portion 30, and thereby when the part 1 is loaded into and unloaded from the storage portion 30, the bulging portion 33 is pushed toward the outside of the cylinder by the part 1, and the storage portion 30 can be thereby bent slightly. Therefore, loading and unloading the part 1 into and from the storage portion 30 can be made easy.

In addition, in the storage portion 30 of the second aspect, the inner size $D_{35}$ of the intermediate portion between the bulging portion 33 in the storage portion 30 and the second opening end portion 32 is larger than the outer size $D_1$ of the part 1, and therefore when the part 1 is stored such that the whole part 1 falls in the storage portion 30, a slight gap can be generated between the inner wall face 30a of the storage portion 30 and the part 1 in the intermediate portion 35. Thereby, steam, a gas, and the like which can be used for a sterilization treatment diffuse around the part 1, and therefore the sterilization treatment can be performed to the part 1 sufficiently and effectively.

Further, in the storage portion 30 of the second aspect, the inner size $D_{33}$ of the bulging portion 33 and the inner size $D_{32}$ of the second opening end portion 32 are smaller than the outer size $D_1$ of the part 1, and therefore when the part 1 is stored in the storage portion 30 such that the whole part 1 falls in the storage portion 30, the bulging portion 33 and the second opening end portion 32 function as a stopper for the part 1. Thereby, unintended detachment of the part 1 stored in the storage portion 30 can be suppressed.

In the bulging portion 33 in the storage portion 30 of the second aspect as well as the bulging portion 33 in the storage portion 30 of the first aspect, the inner wall face 30a of the storage portion 30 on the side of the first opening end portion 31 preferably bulges continuously from the first opening end portion 31 in the direction of the inside of the cylinder, thereby forming an opening widened toward the first opening end portion 31. Thereby, in the size in the direction XY orthogonal to the axial direction Z of the cylinder of the storage portion 30, the first opening end portion 31 having an inner size $D_{31}$ larger than the outer size $D_1$ of the part 1 is easily obtained.

In addition, the storage portion 30 of the second aspect as well as the storage portion 30 of the first aspect is preferably provided with a tapered-off portion 34 where the inner wall face 30a of the storage portion 30 on the side of the second opening end portion 32 is formed in such a way as to narrow toward the second opening portion 32. Thereby, in the size in the direction XY orthogonal to the axial direction Z of the cylinder of the storage portion 30, the second opening end portion 32 having an inner size $D_{32}$ smaller than the outer size $D_1$ of the part 1 is easily obtained. Further, by forming the inner wall face 30a of the storage portion 30 on the side of the second opening end portion 32 in such away as to narrow toward the second opening end portion 32 in the same manner as in the storage portion 30 of the first aspect, there is also a structural advantage in production that there is no need to make the structure of a metal mold for use in producing the holding member 10 by injection molding or the like complicated such that the metal mold is divided at a position where the bulging portion 33 bulges most.

It is to be noted that in the bulging portion 33 in the storage portion 30 of the second aspect, the inner wall face 30a of the storage portion 30 on the side of the first opening end portion 31 may not be continuous from the first opening end portion 31, and the opening widened toward the first opening end portion 31 may not be formed. In addition, the storage portion 30 of the second aspect does not have to be provided with the above-described tapered-off portion 34. The constitution of a holding member 11 provided with a storage portion 36 such as the one described above is illustrated in FIG. 3 as one example of the constitution according to a modified example of the storage portion 30 of the second aspect. The storage portion 36 illustrated in FIG. 3 is provided with: a first opening end portion 31A; a bulging portion 33A formed discontinuously from the first opening end portion 31A on the side of the first opening end portion 31A; and a second opening end portion 32A, wherein an inner wall face 36a of the storage portion 36 is formed into a tapered shape (storage portion 36 has reversely tapered shape) from the first opening end portion 31A toward the second opening end portion 32A.

With respect to the holding member 10 according to one embodiment of the present invention, in the size in the direction XY orthogonal to the axial direction Z of the cylinder of the storage portion 30, the inner size (inner diameter) $D_{31}$ of the first opening end portion 31 is preferably larger than the inner size (inner diameter) $D_{35}$ of the intermediate portion 35 between the bulging portion 33 and the second opening end portion 32. In addition, in the size in the direction XY orthogonal to the axial direction Z of the cylinder of the storage portion 30, the inner size (inner diameter) $D_{32}$ of the second opening end portion 32 is preferably equal to or smaller than the inner size (inner diameter) $D_{33}$ at the position where the bulging portion 33 is provided.

When a case where the part 1 to be stored in the storage portion 30 in the holding member 10 is a piston is given as an example, the inner size $D_{33}$ of the bulging portion 33 is preferably smaller than the minimum value of the tolerance of the outer size $D_1$ of the piston by 0.01 to 0.5 mm (more preferably 0.02 to 0.4 mm, and still more preferably 0.05 to 0.2 mm). In addition, the height of the bulging portion 33 is preferably 0.1 to 0.5 mm, and more preferably 0.1 to 0.3 mm based on the inner wall face 30a at a position corresponding to the inner size $D_{35}$ of the intermediate portion 35.

As illustrated in FIG. 1 and FIG. 2, the holding member 10 is preferably further provided with connection ribs 40 outside the cylinder of each of the storage portions 30, the connection ribs 40 each connecting adjacent storage portions 30 in a plurality of the storage portions 30. In the shape in planar view of the substrate portion 20, the connection ribs 40 illustrated as an example in FIG. 1 include parallel connection ribs 41 each connecting storage portions 30 adjacent in a direction parallel to one side of the substrate portion 20 and inclined connection ribs 42 each connecting the storage portions 30 adjacent in an oblique direction.

A connection rib 40 is formed integrally with the outer wall face 30b of the storage portion 30, and the connection rib 40 as well as the storage portion 30 is preferably provided to be approximately vertical to the first surface 20a of the substrate portion 20. In addition, the connection rib 40 may be provided apart from the first surface 20a of the substrate portion 20 as long as the connection rib 40 connects adjacent storage portions 30 at outer wall faces 30b of the adjacent storage portions 30, or as illustrated in the figure, the connection rib 40 may be stood on the first surface 20a of the substrate portion 20.

As described previously, the holding member 10 may be subjected to conveyance, a sterilization treatment, assembly of a chemical container, and other processes while being in a state in which the part 1 is held in each of a plurality of storage portions 30 in some cases, and therefore load may be applied to the holding member 10 in some cases. To deal with this problem, when the connection ribs 40 are provided in the holding member 10, the strength of the whole holding member 10 can be enhanced and deformation (distortion) of the holding member 10 can be suppressed. Therefore, for example, even when the part 1 stored in the storage portion 30 is perforated using an automatic assembler, the part 1 can be smoothly perforated and a chemical container can be smoothly assembled combining the part 1 with another part.

The connection rib 40 is preferably formed at a position lower than the height from the first surface 20a of the substrate portion 20 to the position of the bulging portion 33 of the storage portion 30 such that the storage portion 30 can be slightly bent as described previously when the part 1 is loaded into and unloaded from the storage portion 30 while the above-described effect of the connection rib 40 is maintained. When the holding member 10 is obtained by injection molding or the like, the product (holding member 10) can be easily released from a metal mold by preparing the connection rib 40 having such height.

As illustrated in FIG. 1, the holding member 10 is preferably further provided with a plurality of supporting pillars 50 each formed on the side of the first surface 20a of the substrate portion 20 in such a way as to protrude higher than the storage portion 30. The supporting pillars 50 are preferably provided such that the holding member 10, when accommodated in a box type container, which will be described later, can stably stand to the bottom face of the box type container or preferably provided at the position and in the number (4 in FIG. 1) of the supporting pillars 50 in consideration of the balance of the strength of the holding member 10, or other properties. When the holding member 10 is provided with a plurality of supporting pillars 50, the storage portion 30 can be thereby made into a non-contact state to a face where the holding member 10 is placed when the holding member 10 is placed with the side of the first face 20a of the substrate portion 20 facing downward. Therefore, a sterilization treatment of the part 1 stored in the state can be performed more effectively.

As a figure for further describing the constitution of a supporting pillar 50, FIG. 4 illustrates an enlarged diagram of the region B illustrated in FIG. 1A, and FIG. 5 illustrates a sectional view taken along the C-C' line in FIG. 4. In addition, FIG. 6 illustrates an enlarged sectional view illustrating a state in the vicinity of supporting pillars 50 at the time when two holding members 10 according to one embodiment of the present invention are stacked.

As illustrated in FIG. 4 and FIG. 5, the holding member 10 is preferably further provided with recessed portions 51 each provided at a position on the side of the second surface 20b of the substrate portion 20, the position corresponding to each of the supporting pillars 50 provided on the side of the surface 20a, in such a way as to be recessed toward an inside of each of the supporting pillars 50. As illustrated in FIG. 6, a supporting pillar 50 of another holding member 10 is accommodated in one of these recessed portions 51. By the holding member 10 provided with the supporting pillars 50 and the recessed portions 51, a plurality of holding members 10 can be easily stacked, and a plurality of holding members 10 can be stacked and accommodated in one box type container.

The supporting pillars 50 each illustrated as an example in FIG. 4 to FIG. 6 are each provided with: a pedestal portion 52 from the substrate portion 20 up to a predetermined height; and a connection portion 53 from the pedestal portion 52 up to the tip, wherein the previously described recessed portion 51 is provided in the pedestal portion 52. The connection portion 53 is formed into a cross square pillar shape, but the shape of the connection portion 53 is not particularly limited and may be an approximately columnar shape, an approximately elliptic column shape, an approximately rectangular, square pillar shape, or the like. In addition, the pedestal portion 52 is formed into an approximately columnar shape, but the shape of the pedestal portion 52 is not particularly limited and may be an approximately elliptic column shape or an approximately square pillar shape.

From the viewpoint of the strength of the supporting pillar 50 and the easiness of stacking the supporting pillars 50, the sectional shapes of the recessed portion 51, the pedestal portion 52, and the connection portion 53 are each preferably an approximately trapezoidal shape, and more preferably an isosceles trapezoidal shape in the longitudinal section of the supporting pillar 50. As the trapezoidal shape of the section of the connection portion 53, an angle $\theta_1$ made by a leg of the trapezoidal shape and a perpendicular line to the substrate portion 20 is preferably 1 to 10 degrees, and more preferably 2 to 7 degrees. As the trapezoidal shapes of the sections of the recessed portion 51 and the pedestal portion 52, an angle $\theta_2$ made by a leg of the trapezoidal shape and a perpendicular line to the substrate portion 20 is preferably 5 to 30 degrees, and more preferably 10 to 20 degrees.

As illustrated in FIG. 6, a depth $H_{51}$ of the recessed portion 51 from the second surface 20b of the substrate portion 20 is preferably smaller than a difference ($H_{50}-H_{30}$) between a height $H_{50}$ of the supporting pillar 50 from the second surface 20b of the substrate portion 20 and a height $H_{30}$ of the storage portion 30 from the second surface 20b ($H_{51}<H_{50}-H_{30}$). Thereby, when a plurality of holding members 10 are stacked using the supporting pillars 50 and the recessed portions 51, the storage portion 30 of one holding member 10 can be made into a non-contact state to another holding member 10, and a gap can be formed between the holding members 10. It becomes easy for steam or a gas to flow in the gap, and therefore a sterilization treatment can be performed more effectively in a state in which a plurality of holding members 10 are stacked.

In addition, the depth $H_{51}$ of the recessed portion 51 is preferably 20 to 50% (0.2 to 0.5 times the $H_{50}$), and more preferably 30 to 40% (0.3 to 0.4 times the $H_{50}$) of the height $H_{50}$ of the supporting pillar 50. Further, the depth $H_{51}$ of the recessed portion 51 is preferably 60 to 99% (0.6 to 0.99 times the difference described later), more preferably 70 to 95% (0.7 to 0.95 times the difference described later), and still more preferably 70 to 90% (0.7 to 0.9 times the difference described later) of a difference between the height $H_{50}$ of the supporting pillar 50 and the height $H_{30}$ of the storage portion 30 ($H_{50}-H_{30}$).

By making the constitution of the depth $H_{51}$ of the recessed portion 51 as described above in consideration of the relationship with the height $H_{50}$ of the supporting pillar 50 and the height $H_{30}$ of the storage portion 30, the gap between the storage portion 30 of one holding member 10 and another holding member 10 can be made smaller when a plurality of holding members 10 are stacked using the supporting pillars 50 and the recessed portions 51. Therefore, when the holding members 10 are stacked and accommodated in a box type container, which will be described later, the number of holding members 10 which can be accommodated can be increased, and about 7 holding members 10 can be stacked in one box type container. Specifically, the gap is preferably 0.1 to 4 mm, more preferably 0.5 to 3 mm, and still more preferably 1 to 3 mm.

As described above in detail, the holding member 10 according to one embodiment of the present invention is provided with any one or both of the constitution of the first aspect and the constitution of the second aspect, and therefore the part 1 is easily loaded into and unloaded from the storage portion 30, and sudden detachment of the part 1 from the storage portion 30 can be suppressed. In addition, by using this holding member 10, a sterilization treatment of the part 1 can be performed effectively. Further, this holding member 10, as will be described next, can be provided for storage, conveyance, and a sterilization treatment of the chemical container part 1, and assembly into a chemical container, and other processes as a packaging structure in which the holding member 10 is accommodated, in a state of holding chemical container parts 1, in a box type container.

<Packaging Structure of Chemical Container Parts>

FIG. 7 is a perspective view illustrating one example of a box type container 7 which can be used for a packaging structure of chemical container parts according to one embodiment of the present invention. FIG. 8 is a plan view of a packaging structure 100 using the box type container 7 illustrated in FIG. 7, the plan view viewed from a side of an opening portion 7a of the box type container 7. As illustrated in FIG. 7 and FIG. 8, the packaging structure 100 of chemical container parts according to one embodiment of the present invention is provided with: the box type container 7 having the opening portion 7a; the holding member 10 according to the previously described embodiment accommodated in the box type container 7; and the chemical container parts 1 stored in the storage portions 30 in the holding member 10.

When the packaging structure 100 is used, a plurality of parts 1 can be thereby provided for conveyance, a sterilization treatment, and the like in a state in which the plurality of parts 1 are stored in the storage portions 30 in the holding member 10. Steam, a gas, or the like can be filled in an inside 7b of the box type container 7, and therefore by using the box type container 7, a sterilization treatment can be performed more effectively.

The shape of the box type container 7 is not particularly limited as long as the shape is a box (basket) type which has the opening portion 7a to be a loading and unloading mouth for the holding member 10 at an upper portion and in which the holding member 10 can be accommodated in the inside 7b. The planar shape of the box type container 7 is usually an approximately rectangular shape, but may be an approximately circular shape, an approximately elliptical shape, an approximately polygonal shape, or the like. Also, the material of the box type container 7 is not particularly limited, and the box type container 7 is usually made of a synthetic resin but may be made of a metal, or a composite material of a metal and a synthetic resin or the like. A recessed or protruded shape (swelled shape or depressed shape) is preferably provided at a bottom portion 7c or a side face 7e of the box type container 7 in order to enhance the strength of the box type container 7, thereby preventing deformation.

When the holding member 10 is accommodated in the box type container 7, the holding member 10 is preferably accommodated in the box type container 7 such that the side of the first surface 20a of the substrate portion 20 in the holding member 10 oppositely faces the bottom face (inner face of bottom portion 7c) of the box type container 7. A plurality of (two or more) holding members 10 are preferably stacked and accommodated in the box type container 7, and for example, about 2 to about 7 holding members 10 are preferably stacked and accommodated in the box type container 7. In a case where the holding member 10 is provided with the previously described supporting pillars 50 and recessed portions 51, a plurality of holding members 10 can be stacked by combining the recessed portions 51 of one holding member 10 and the supporting pillars 50 of another holding member 10, and therefore about 7 holding members 10 can be stacked in one box type container 7.

In addition, when two or more holding members 10 are stacked, the storage portion 30 of the holding member 10 can be made into a non-contact state to another holding member 10, as described previously. Therefore, also, in a state in which a plurality of holding members 10 are accommodated in the box type container 7, an effective sterilization treatment can also be performed to the parts 1 stored in the storage portions 30.

The packaging structure 100 is preferably further provided with a gas impermeable film (not illustrated in figures) sealing the opening portion 7a of the box type container 7. The gas impermeable film can seal the opening portion 7a at the upper portion of the box type container 7 by releasably sealing a ring-shaped flange portion 7d of the box type container 7. As the gas impermeable film, a high-density polyethylene film, a polyethylene terephthalate film, and the like, and a laminated film or the like of a plurality of resin films including at least any one of the films can be used.

In addition, by releasably sealing the ring-shaped portion 7d of the box type container 7 with a sterilizable film, further, covering the whole box type container 7 with a gas impermeable film, and then sucking the air inside the impermeable film, the box type container 7 can be wrapped and the opening portion 7a can also be sealed. The sterilizable film is a film which permeates gases for sterilization, such as a gas and steam, but does not permeate germs, and the sterilizable film is constituted, for example, by a filament of high-density polyethylene or other polymers. As the sterilizable film, Tyvek® manufactured by E.I. du Pont De Nemours and Company, and the like can be used.

As described above, the holding member according to one embodiment of the present invention can have the following constitution.

[1] A holding member provided with: a sheet-like substrate portion having a first surface and a second surface; and a plurality of storage portions each penetrating the first surface and the second surface of the substrate portion and each protruding in a direction of a side of the first surface and in a form of a cylinder where a chemical container part is to be stored, wherein the storage portions are each provided with: a first opening end portion forming a loading and unloading mouth for the part at a protruded tip of each of the storage portions; a bulging portion where an inner wall face of each of the storage portions on a side of the first opening end portion bulges continuously from the first opening end portion in a direction of an inside of the cylinder, thereby forming an opening widened toward the first opening end portion; a second opening end portion formed at a base end of each of the storage portions by the second surface of the substrate portion; and a tapered-off portion where the inner wall face of each of the storage portions on a side of the second opening end portion is formed in such a way as to narrow toward the second opening end portion.

[2] A holding member provided with: a sheet-like substrate portion having a first surface and a second surface; and a plurality of storage portions each penetrating the first surface and the second surface of the substrate portion and each protruding in a direction of a side of the first surface and in a form of a cylinder where a chemical container part is to be stored, wherein the storage portions each comprise: a first opening end portion forming a loading and unloading mouth for the part at a protruded tip of each of the storage portions; a bulging portion where an inner wall face of each of the storage portions on a side of the first opening end portion bulges in a direction of an inside of the cylinder; and a second opening end portion formed at a base end of each of the storage portions by the second surface of the substrate portion, and in a size in a direction orthogonal to an axial direction of the cylinder of each of the storage portions, an inner size of the first opening end portion and an inner size of an intermediate portion between the bulging portion and the second opening end portion are larger than an outer size of the part, and an inner size at a position where the bulging portion is provided and an inner size of the second opening end portion are smaller than the outer size of the part.

[3] The holding member according to [2], wherein in the bulging portion, an inner wall face of each of the storage portions on a side of the first opening end portion bulges continuously from the first opening end portion in a direction of an inside of the cylinder, thereby forming an opening widened toward the first opening end portion.

[4] The holding member according to [2] or [3], wherein the storage portions are each provided with a tapered-off portion where the inner wall face of each of the storage portions on a side of the second opening end portion is formed in such a way as to narrow toward the second opening end portion.

[5] The holding member according to any one of [1] to [4], wherein in a size in a direction orthogonal to an axial direction of the cylinder of each of the storage portions, an inner size of the first opening end portion is larger than an inner size of an intermediate portion between the bulging portion and the second opening end portion.

[6] The holding member according to any one of [1] to [5], wherein in a size in a direction orthogonal to an axial direction of the cylinder of each of the storage portions, an inner size of the second opening end portion is equal to or smaller than an inner size at a position where the bulging portion is provided.

[7] The holding member according to any one of [1] to [6], further provided with connection libs outside the cylinder of each of the storage portions, the connection libs each connecting adjacent storage portions in a plurality of the storage portions, wherein the connection libs are each formed at a position lower than a height from the first surface of the substrate portion to the bulging portion of each of the storage portions.

[8] The holding member according to any one of [1] to [7], further provided with a plurality of supporting pillars each formed on a side of the first surface of the substrate portion in such a way as to protrude higher than each of the storage portions.

[9] The holding member according to [8], further provided with recessed portions for storing the supporting pillars of another holding member, the recessed portions each provided at a position on a side of the second surface of the substrate portion, the position corresponding to each of the supporting pillars provided on the side of the first surface, in such a way as to be recessed toward an inside of each of the supporting pillars.

[10] The holding member according to any one of [1] to [9], wherein the part is a syringe piston.

In addition, the packaging structure of chemical container parts according to one embodiment of the present invention can have the following constitution.

[11] A packaging structure of chemical container parts, the packaging structure provided with: a box type container having an opening portion; the holding member according to any one of [1] to [10] accommodated in the box type container; and chemical container parts stored in the storage portions in the holding member.

What is claimed is:

1. A holding member that is configured to hold a plurality of syringe pistons, the holding member comprising:
   a sheet-shaped substrate portion having a first surface and a second surface;
   a plurality of storage portions each penetrating the first surface and the second surface of the substrate portion and each protruding in a direction of a side of the first surface and in a form of a cylinder, and each storage portion being configured to store an entire portion of one of the plurality of the syringe pistons therein; and
   a plurality of connection ribs located outside the cylinder of each of the plurality of the storage portions, the plurality of the connection ribs each connecting the storage portions adjacent to each other among the plurality of the storage portions,
   wherein the plurality of the storage portions each comprises:
      a first opening end portion forming a loading and unloading mouth for the one of the plurality of the syringe pistons at a protruded tip of each of the plurality of the storage portions;
      a bulging portion where an inner wall face of each of the plurality of the storage portions on a side of the first opening end portion bulges continuously from the first opening end portion in a direction of an inside of the cylinder, thereby forming an opening widened toward the first opening end portion;
      a second opening end portion formed at a base end of each of the plurality of the storage portions by the second surface of the substrate portion; and
      a tapered-off portion where the inner wall face of each of the plurality of the storage portions on a side of the second opening end portion is formed in such a way as to narrow an opening toward the second opening end portion, and
   wherein each of the plurality of the connection ribs is formed at a position lower than a height of the bulging portion of each of the plurality of the storage portions from the first surface of the substrate portion.

2. The holding member according to claim 1,
   wherein in a size in a direction orthogonal to an axial direction of the cylinder of each of the plurality of the storage portions, an inner size of the first opening end portion is larger than an inner size of an intermediate portion between the bulging portion and the second opening end portion.

3. The holding member according to claim 1,
   wherein in a size in a direction orthogonal to an axial direction of the cylinder of each of the plurality of the storage portions, an inner size of the second opening end portion is equal to or smaller than an inner size at a position where the bulging portion is provided.

4. The holding member according to claim 1, further comprising a plurality of supporting pillars each formed on the side of the first surface of the substrate portion in such a way as to protrude higher than each of the plurality of the storage portions.

5. The holding member according to claim 4, further comprising recessed portions for storing the plurality of the supporting pillars of another holding member, the recessed portions each provided at a position on a side of the second surface of the substrate portion, the position corresponding to each of the plurality of the supporting pillars provided on the side of the first surface, in such a way as to be recessed toward an inside of each of the plurality of the supporting pillars.

6. A packaging structure of chemical container parts, the packaging structure comprising:
a box type container having an opening portion;
the holding member according to claim 1 accommodated in the box type container; and
the plurality of the syringe pistons stored in the plurality of the storage portions in the holding member.

7. A holding member that is configured to hold a plurality of syringe pistons, the holding member comprising:
a sheet-shaped substrate portion having a first surface and a second surface;
a plurality of storage portions each penetrating the first surface and the second surface of the substrate portion and each protruding in a direction of a side of the first surface and in a form of a cylinder, and each storage portion being configured to store an entire portion of one of the plurality of the syringe pistons in the each of the plurality of the storage portions; and
a plurality of connection ribs located outside the cylinder of each of the plurality of the storage portions, the plurality of the connection ribs each connecting the storage portions adjacent to each other among the plurality of the storage portions,
wherein each of the plurality of the storage portions comprises:
a first opening end portion forming a loading and unloading mouth for the one of the plurality of the syringe pistons at a protruded tip of each of the plurality of the storage portions;
a bulging portion where an inner wall face of each of the plurality of the storage portions on a side of the first opening end portion bulges in a direction of an inside of the cylinder; and
a second opening end portion formed at a base end of each of the plurality of the storage portions by the second surface of the substrate portion, and
wherein in a size in a direction orthogonal to an axial direction of the cylinder of each of the plurality of the storage portions, an inner size of the first opening end portion and an inner size of an intermediate portion between the bulging portion and the second opening end portion are configured to be larger than an outer size of the one of the plurality of the syringe pistons, and an inner size at a position where the bulging portion is provided and an inner size of the second opening end portion are configured to be smaller than the outer size of the one of the plurality of the syringe pistons, and
wherein each of the plurality of the connection ribs is formed at a position lower than a height of the bulging portion of each of the plurality of the storage portions from the first surface of the substrate portion.

8. The holding member according to claim 7,
wherein in the bulging portion, an inner wall face of each of the plurality of the storage portions on the side of the first opening end portion bulges continuously from the first opening end portion in the direction of the inside of the cylinder, thereby forming the opening widened toward the first opening end portion.

9. The holding member according to claim 7,
wherein the plurality of the storage portions each comprises a tapered-off portion where the inner wall face of each of the plurality of the storage portions on a side of the second opening end portion is formed in such a way as to narrow an opening toward the second opening end portion.

10. The holding member according to claim 7,
wherein in the size in the direction orthogonal to the axial direction of the cylinder of each of the plurality of the storage portions, the inner size of the first opening end portion is larger than the inner size of the intermediate portion between the bulging portion and the second opening end portion.

11. The holding member according to claim 7,
wherein in the size in the direction orthogonal to the axial direction of the cylinder of each of the plurality of the storage portions, the inner size of the second opening end portion is equal to or smaller than the inner size at a position where the bulging portion is provided.

12. The holding member according to claim 7, further comprising a plurality of supporting pillars each formed on the side of the first surface of the substrate portion in such a way as to protrude higher than each of the plurality of the storage portions.

13. The holding member according to claim 12, further comprising recessed portions for storing the plurality of the supporting pillars of another holding member, the recessed portions each provided at a position on a side of the second surface of the substrate portion, the position corresponding to each of the plurality of the supporting pillars provided on the side of the first surface, in such a way as to be recessed toward an inside of each of the plurality of the supporting pillars.

14. A packaging structure of chemical container parts, the packaging structure comprising:
a box type container having an opening portion;
the holding member according to claim 7 accommodated in the box type container; and
the plurality of the syringe pistons stored in the plurality of the storage portions in the holding member.

* * * * *